United States Patent
Orth et al.

(10) Patent No.: US 7,982,731 B2
(45) Date of Patent: Jul. 19, 2011

(54) METHOD OF PROCESSING A DIGITIZED WORKPIECE, PARTICULARLY A THREE-DIMENSIONAL MODEL OF A DENTAL PROSTHETIC ITEM TO BE PRODUCED THEREFROM, AND APPARATUS THEREFOR

(75) Inventors: Ulrich Orth, Lautertal (DE); Volker Wedler, Hirschberg (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 11/186,833

(22) Filed: Jul. 22, 2005

(65) Prior Publication Data

US 2006/0020363 A1 Jan. 26, 2006

(30) Foreign Application Priority Data

Jul. 23, 2004 (DE) .......................... 10 2004 035 970

(51) Int. Cl.
*G06T 15/00* (2011.01)
*G09G 5/00* (2006.01)

(52) U.S. Cl. ........................................ 345/419; 345/420

(58) Field of Classification Search .................. 345/419, 345/421, 423, 428, 619, 629, 631, 640, 647, 345/650, 653, 660, 664, 679, 420, 630; 433/6, 433/18, 20, 24; 700/117, 187
See application file for complete search history.

(56) References Cited

U.S. PATENT DOCUMENTS

| | | | |
|---|---|---|---|
| 5,257,203 A | 10/1993 | Riley et al. | |
| 5,557,719 A | 9/1996 | Ooka et al. | |
| 5,615,319 A | 3/1997 | Metzger et al. | |
| 6,174,168 B1 | 1/2001 | Dehoff et al. | |
| 6,454,629 B1 | 9/2002 | Basler et al. | |
| 6,488,503 B1 * | 12/2002 | Lichkus et al. | 433/202.1 |
| 6,691,764 B2 * | 2/2004 | Embert et al. | 164/4.1 |
| 7,034,818 B2 * | 4/2006 | Perry et al. | 345/419 |
| 7,234,937 B2 * | 6/2007 | Sachdeva et al. | 433/24 |
| 2002/0180760 A1 * | 12/2002 | Rubbert et al. | 345/630 |
| 2006/0063135 A1 | 3/2006 | Mehl | |

FOREIGN PATENT DOCUMENTS

CA 2517927 9/2004

* cited by examiner

*Primary Examiner* — Amare Mengistu
*Assistant Examiner* — Aaron M Guertin
(74) *Attorney, Agent, or Firm* — Fitzpatrick, Cella, Harper & Scinto

(57) ABSTRACT

In a method of processing a digitized workpiece (1), especially a three-dimensional model of a dental prosthetic item to be produced therefrom, by altering the surface data of the workpiece by means of a tool which acts on a local zone of action (3) on the surface (2), a change in height of said surface (2) is effected in said zone of action (3) of said tool when the tool is applied to said surface, the said zone of action of said tool covering a modified region (5) showing a substantially constant change in height (t) over the zone of action (3) and also a transition region (4), in which the surface of the modified region (5) merges into the surface surrounding said zone of action (3).

11 Claims, 7 Drawing Sheets

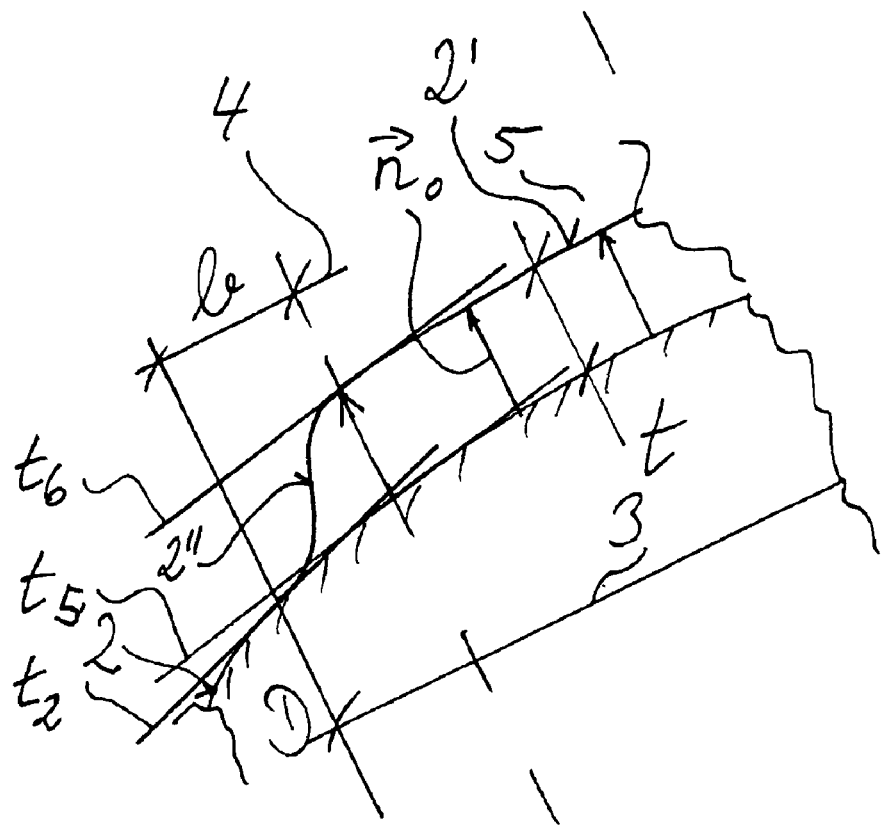
FIG. 7
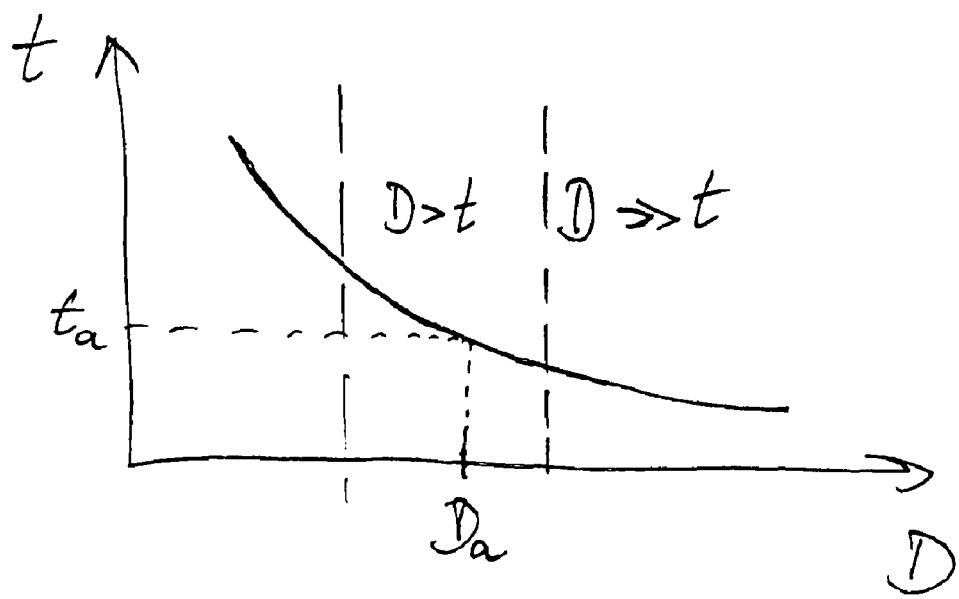
Fig: 9

METHOD OF PROCESSING A DIGITIZED WORKPIECE, PARTICULARLY A THREE-DIMENSIONAL MODEL OF A DENTAL PROSTHETIC ITEM TO BE PRODUCED THEREFROM, AND APPARATUS THEREFOR

BACKGROUND OF THE INVENTION

1. Field of the Invention

The invention relates to a method of processing a digitized workpiece, particularly a three-dimensional model of a dental prosthetic item to be produced therefrom, by altering the surface data of the workpiece by means of a tool which acts on a local zone of action on the surface.

A design being processed by CAD is not constrained by the limitations of the physical characteristics of materials and tools, indeed, the operation of the tool can completely free itself from these characteristics and overcome their disadvantages. It is desired, in particular, to improve the operability thereof.

Existing dental CAD/CAM systems offer no free-form tools that go beyond the techniques used in conventional dental technology. Thus these free-form tools, like those used in manual processing of physical models, have the disadvantage that the fine structures of the surface are obliterated due to the application of wax.

2. Description of the Related Art

In dental CAD/CAM systems, various tools are used for designing models for the fabrication of dental prosthetic items. Using these tools, the digital model of the dental prosthetic item can typically be modified on a line or point basis. For example, the equatorial line can be changed, the whole model can be rescaled or displaced, individual cusps can be made higher or lower, or the site of a cusp point can be shifted.

Furthermore, tools are used with which one can freely change the shape of the surface and which are derived from techniques of conventional dental technology, for example, the application of drops of wax or the removal of material with a knife, both realized of course in a digital form.

The line-based or point-based tools are usually easy to use, but they have the disadvantage that the user can only insufficiently and indirectly influence the surface between the lines or points.

The tools derived from conventional dental technology are typically oriented toward the characteristics of mechanical tools like, for example, a knife, or toward the characteristics of wax, for example its drop size or its temperature.

It is an object of the invention to provide the user of CAD/CAM systems with a tool that gives him additional possibilities in designing the shape of models.

SUMMARY AND OBJECTS OF THE INVENTION

The method proposed herein for processing a digitized workpiece, especially a three-dimensional model of a dental prosthetic item to be produced therefrom, by altering the surface data of the workpiece by means of a tool operating on a local zone of action on the surface, consists in applying the tool to the surface to produce a change in height in the zone of action of the tool, the said zone of action of the tool covering a modified region showing a substantially constant change in height over the said zone of action, as well as a transition region in which the surface of the modified region merges into the surface surrounding the zone of action.

The tool proposed herein enables the user to apply or remove a thin layer of material of substantially constant layer thickness (hereafter referred to as a "change in height") at an arbitrary point on the surface. The size of the region is adjustable. By using a repeat function when moving the tool over the same place on the surface, the user can build up and/or clear away tooth structures in a simple way, without obliterating the fine structural features.

By decoupling from the paradigm of conventional dental techniques, new possibilities for the design of dental prosthetic items arise. The user can effect better control of the change in shape than with currently available tools whilst retaining existing fine structural features.

The ratio of the change in height in the zone of action to the extent of the zone of action is at most 1:50, and preferably between 1:100 and 1:200. It is advantageous for the ratio of the thickness of the change in height to the extent of the zone of action to be 1:140. This allows for sufficiently fine processing without destroying fine structural features.

It is advantageous for the ratio of the width of the transition region of the zone of action to the change in height to be between 1:1 and 20:1. This allows for a sufficiently smooth transition.

The position of the tool can be advantageously represented by a cursor that is movable over the image of the surface of the workpiece, and which corresponds to a selected region of the surface. The selected region can be independent of the zone of action of the tool.

The surface covered by the zone of action will be changed by means of the tool in the direction of a vector normal to the surface.

The direction of the change of the surface in the zone of action can be derived, in particular, from a normal vector averaged over an evaluation zone of the tool. The evaluation zone can span all or a part of the zone of action, the modified region, or the selected region.

It is preferable that the normal vector be calculated from a selected region in which the ratio of the selected region to the entire region is between 1:5 and 1:200.

The change in height can consist of either an augmentation or a reduction of material, and a means for choosing the direction of the change in height is provided.

The choice of the direction of the change in height can be indicated by various representations of the tool. The currently activated mode of the tool is then immediately recognizable to the user from the monitor screen.

It may be advantageous to visibly distinguish the region already processed by the tool from the representation of the surface of the model. The user will thus know which region of the surface has already been processed. Furthermore, frequently processed surfaces can be shown differently from once processed surfaces, for example by colored hatching.

It is advantageous for the size of the zone of action to be variable. For that reason, means for displaying the size of the zone of action are provided. In particular, the size of the zone of action can be displayed by colored marking on the surface of the model. The user can enlarge or diminish the zone of action.

It is preferred that the degree of the change in height will depend on the extent of the zone of action. In particular, the change in height can decline with increasing size of the zone of action.

Another object of the invention is a device having means for carrying out the method.

BRIEF DESCRIPTION OF THE DRAWINGS

The method of the invention will be explained below with reference to the following diagrams, in which

FIG. 7 shows in detail the profile of the change in a transition region;

FIG. 9 shows a diagrammatic relationship between the area of the zone of action of the tool and the change in height.

DESCRIPTION OF AN EMBODIMENT OF THE INVENTION

Figure 1:
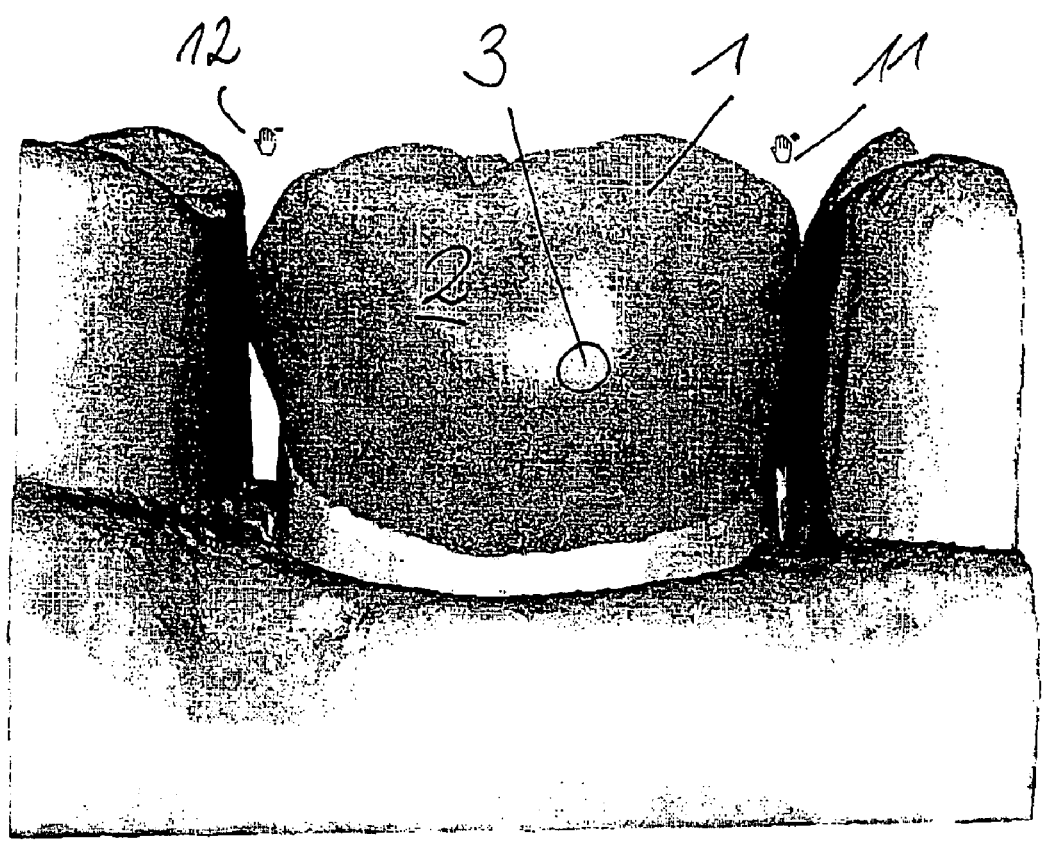
FIG. 1 shows a digitized workpiece in the form of a three-dimensional model of a dental prosthetic item, indicating the region being processed.

FIG. 1 shows a digitized workpiece in the form of a three-dimensional model of a dental prosthetic item for production therefrom, which is to be altered by the user. The model is shown on the monitor of a computer.

During processing, the surface 2 of the model of the dental prosthetic item, present in the form of digital data, will be processed by a tool which influences the design, ie, influences these data. The tool acts on a local zone of action 3 on the surface 2. The zone of action 3 is shown as a circle, but can have other suitable shapes.

Input means, not shown in the figure, are provided for moving the zone of action 3 of the tool over surface 2. Examples thereof are a computer mouse or a digital pen plotter which controls a cursor 11 or 12. The tool is initially free to move over the surface of the representation and can be activated as needed. This happens for example by a mouse-click at a particular place or by clicking and holding a mouse button while at the same time dragging it from a starting point.

The choice of the direction of the change in height is indicated by different depictions of cursor 11 or 12 of the tool; cursor 11, shown as a hand with a plus sign, indicates material deposition, and cursor 12, as a hand with a minus sign, indicates material removal. The currently activated mode of the tool is then immediately recognizable to the user from which of the cursors 11 and 12 is displayed. Contrary to the figure, only one of the two cursors 11 or 12 will be displayed to the user at any one time.

The direction of the change in height may be chosen by a selection device. Switching between deposition and removal of material to produce a change in height of the surface can, for example, be done by pressing the space bar on a computer keyboard.

Figure 2:
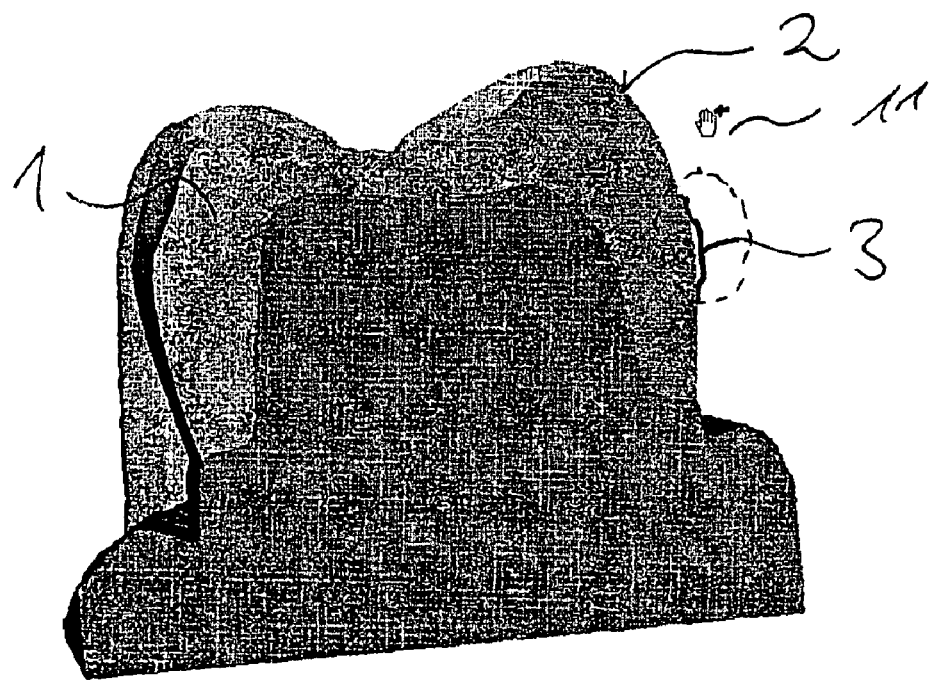
FIG. 2 shows a section of the workpiece of FIG. 1 in the zone of action of the tool.

FIG. 2 shows the dental prosthetic item in transverse cross-section, taken through the zone of action 3 of FIG. 1. Note the shape of surface 2, which is calculated from the surface data and displayed, and note also the change carried out on the surface within the zone of action 3 by means of the tool in deposition mode, as indicated by the cursor 11.

Figure 3A:
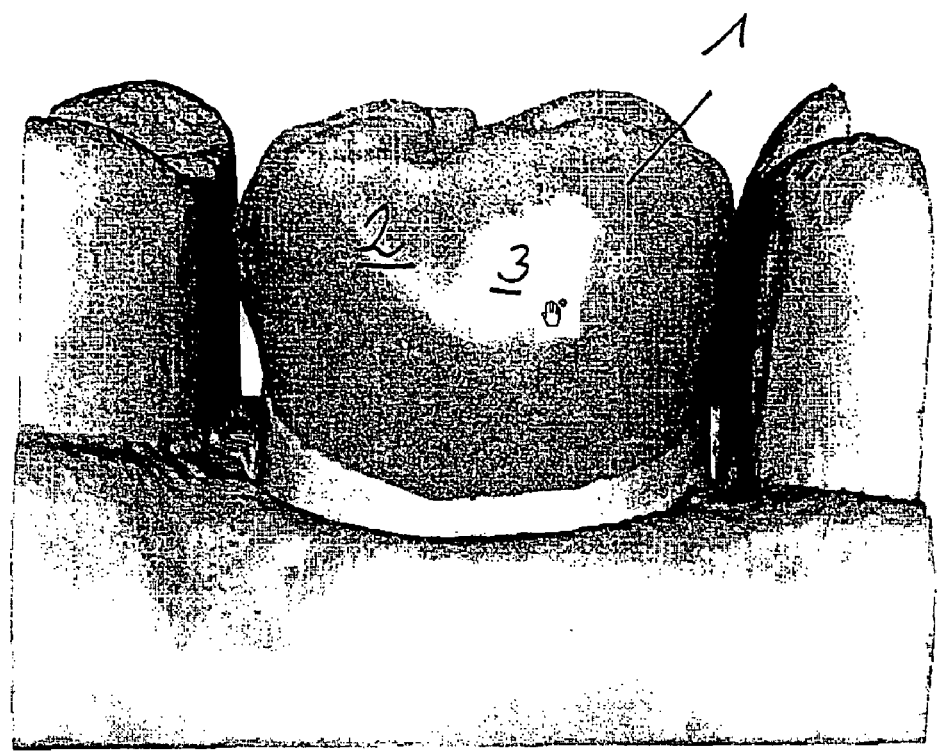
FIG. 3A shows the digital model of the dental prosthetic item of FIG. 1 with the zone of action 3 of the tool on the surface 2.

In FIG. 3A the digital model of the dental prosthetic item of FIG. 1 is shown with the zone of action 3 of the tool on the surface 2 around the cursor 11, the extent of the zone of action 3 being indicated by marking the surface 2, here by using a different color. Representation using a patterned texture, like hatching, is also possible. The user can enlarge or reduce the zone of action 3. For this purpose, means for changing the size of the zone of action are provided.

Figure 3B:
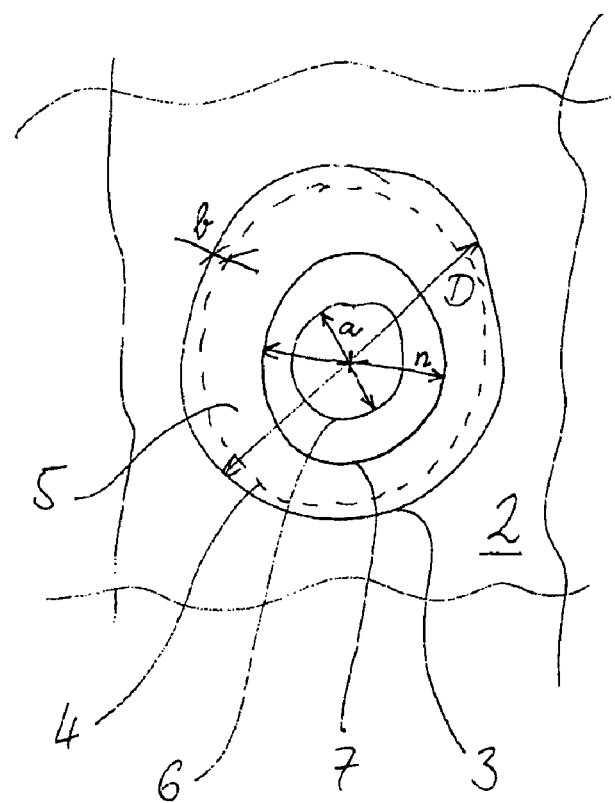
FIG. 3B is an illustrative sketch of the zone of action of the tool as well as other relevant regions.

In FIG. 3B, an illustrative sketch, shows the zone of action 3, as well as other relevant regions, on a subregion of surface 2. The zone of action is shown as a circle, but can also take on other appropriate shapes. In principle, all smoothly-bordered surfaces are possible, with elliptical shapes being preferred, as they present no corners.

The zone of action 3 has an extent D, and surrounding the zone of action 3, no change to the surface 2 takes place.

A transition region 4 is located within the zone of action 3 and has a width b; in the present example it is concentric with the zone of action 3 and centered about a midpoint M.

The transition region 4 merges into a modified region 5 which shows a substantially constant change in height.

The position of the tool is represented by a cursor, as in FIG. 3A, to which a selected region 6 is assigned. This selected region, of diameter a, is independent of the zone of action of the tool; however, in the exemplary embodiment, it is concentric with the zone of action 3.

When using line widths, brushes, or sprays as image-processing tools, it is known that the diameter of the selected region fits the diameter of the zone of action, so that, for example, the line width, the brush width, or the width of the spray stream entails a change in the size of the selected region of the cursor. Similar presetting can be made by the user, with the possibility of changing it.

In order to make the surface area of the regions that have already been processed clearly visible, the zone of action 3 with its extent D can be highlighted with color against surface 2, without immediately displaying the change in height.

Alternatively, it is possible to show the effect of the tool by recomputing the processed regions and displaying the new, changed model, since the display of the model of the dental prosthetic item in FIG. 1 already has reflections and shadings, and changes may be determined simply by altering the reflections and/or shadings as a consequence of the application of the tool. The intermediate step involving an initially two-dimensional representation is then superfluous.

Finally, an evaluation region 7 is provided, which extends over a distance n, and within which a normal vector $n_0$, determining the direction of the change in height, will be constructed from the vectors normal to the surface 2 within the evaluation region, for example by averaging over the evaluation region. In the exemplary embodiment, the evaluation region 7 is also concentric with the zone of action 3, but its extent n is independent of the zone of action 3 and the selected region 6, so that even using a cursor with a small evaluation region 6 and a setting with a large zone of action 3, the evaluation region 7 is unchanged. Obviously the evaluation region can also be adjusted to fit the zone of action. Experience has shown it to be practical to make the evaluation region at least as large as the selected region but not larger than the zone of action.

Figure 4A:
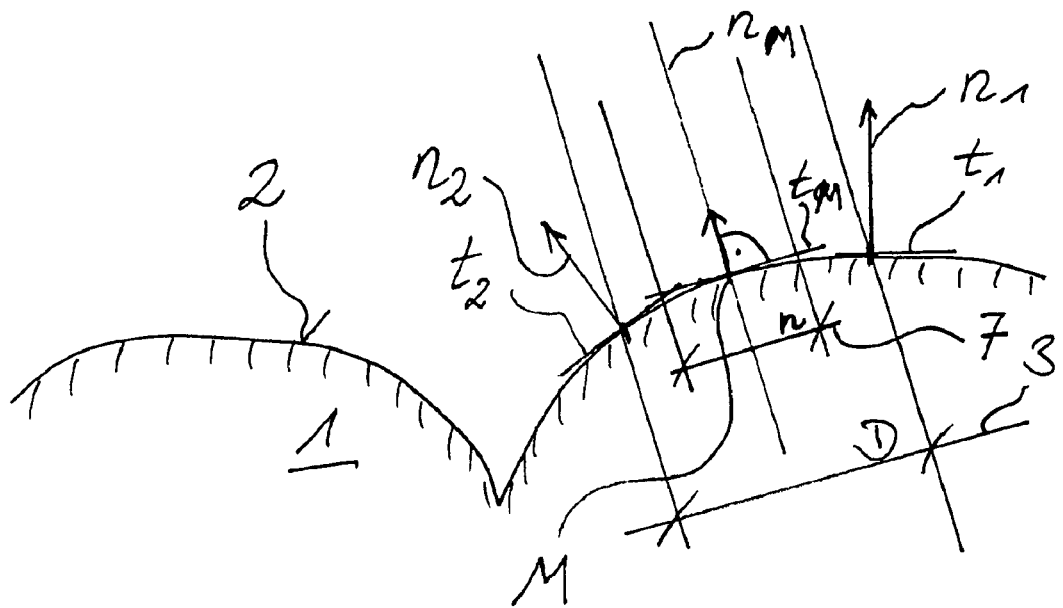
FIG. 4A shows a segment of the workpiece surface and the zone of action of the tool.

In FIG. 4A the division of the surface 2 into different regions, as defined in FIG. 3, is shown diagrammatically in a sectional drawing following FIG. 2.

Here the dental prosthetic item 1 is shown with its surface 2, on which the zone of action 3 is indicated by virtual boundary lines separated from each other by a distance D. The boundaries of the zone 3 are fixed by a distance from a midpoint M, which is part of the surface 2. The normal vector $n_M$ will be determined at the midpoint M, for example by determining the tangent $t_M$ to the surface 2 at the point M.

The value of the normal vector is of secondary importance in the present method, as the change in height is definable as a pre-setting irrespective of the curvature of the surface, and it remains the same during processing of different locations on the surface 2. In this way the user will achieve an estimable change in height by using the tool.

Figure 4B:
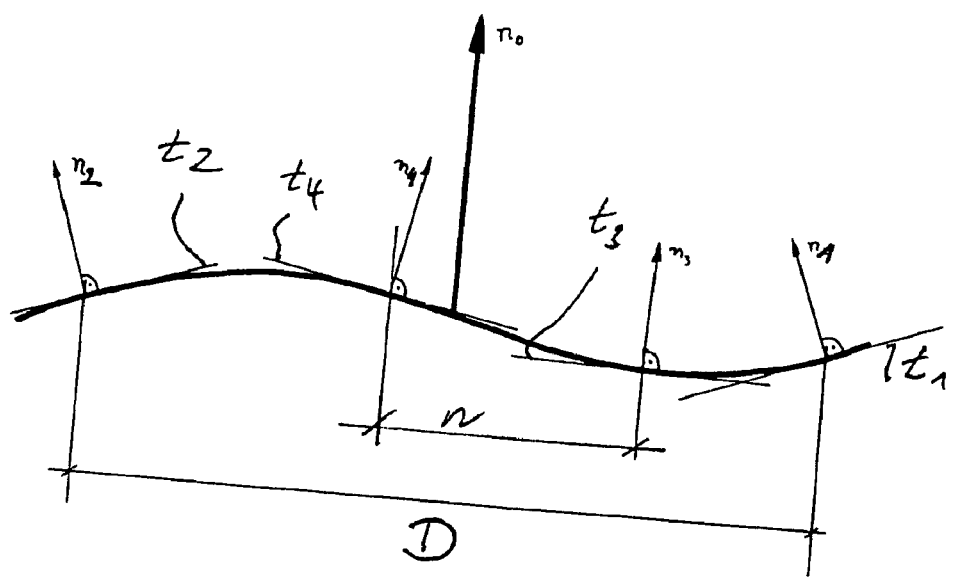
FIG. 4B shows a segment of FIG. 4A.

Also shown are the tangents $t_1$, $t_2$ as well as their normal vectors $n_1$, $n_2$ at the edge of the zone of action 3 of the tool. From these it is clear that the normal vector, in the case of a curved surface 2, takes on different directions over the extent D of the zone of action. However, for the determination of the direction of the change in height in the zone of action 3, and thus of the normal vector $n_0$, only the evaluation region, with an extent of n, will be used; this is shown in detail in FIG. 4B, with the tangents $t_3$, $t_4$, as well as their normal vectors $n_3$, $n_4$, on the border of the evaluation region having an extent of n.

Figure 5:
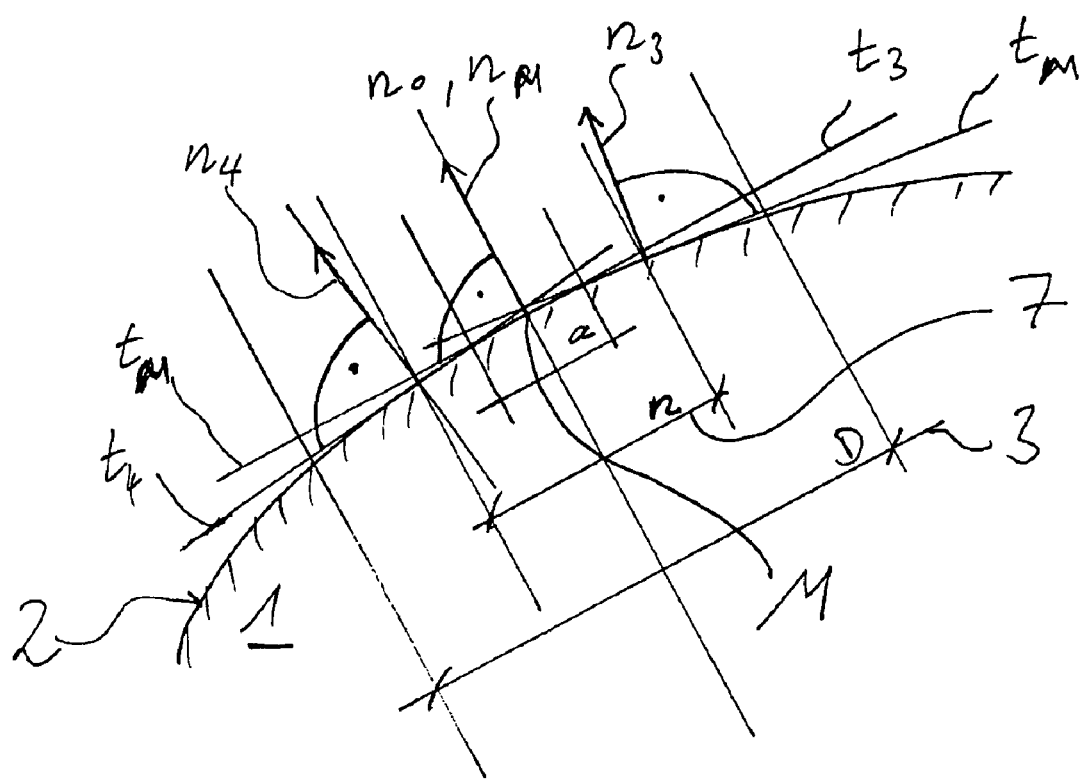
FIG. 5 shows an enlargement of the zone of action of the tool of FIG. 4A, for determining the direction of the change.

This is further clarified in FIG. 5. Here again, on the surface 2 of the dental prosthetic item 1, there is shown the zone of action 3 with its extent D about the midpoint M. Over the evaluation region, an average is made of the direction of the normal vectors $n_M$, $n_3$, $n_4$, which are derived from the tangents $t_M$, $t_3$, $t_4$ to the surface 2. The normal vector $n_0$ resulting from this averaging coincides in the exemplary embodiment with $n_M$. The determination of a normal vector from a selected region with an extent smaller than the extent of the zone of action yields obvious advantages as regards computation effort. In the event that sufficient computing power is available, the normal vector can be evaluated over a larger region, if desired.

On surfaces showing marked local curvature, a larger region leads to greater smoothing of the normal vector and, on the whole, to a more stable procedure. On slightly curved surfaces, the smoothing leads to similar directions of the normal vector, in spite of different regions of the surface having different normal vector directions being selected, so that the direction of the change is not as controllable as when a smaller evaluation region is used.

Figure 6A:
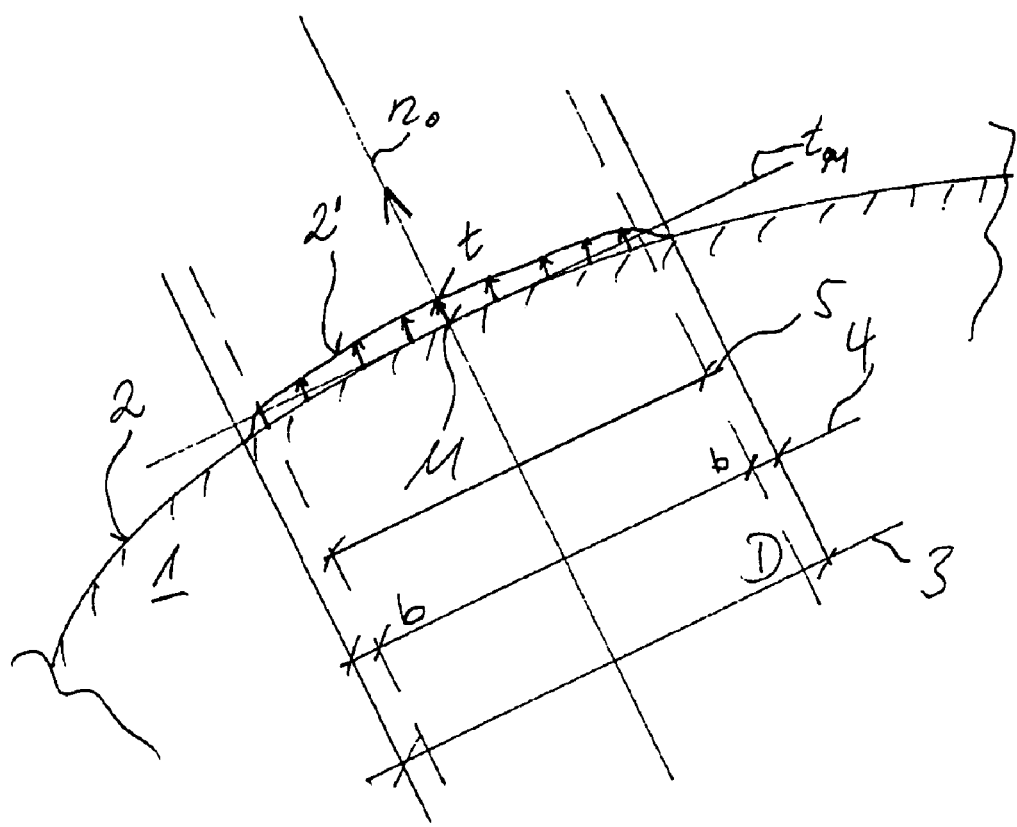
FIG. 6A shows in detail a modification of a surface made with the tool.

In FIG. 6A the change of the surface 2 through the use of the tool is shown in detail. Within the zone of action 3, excluding the transition region 4 of extent b, a constant change in height t of the surface 2 of the dental prosthetic item 1 is carried out over the entire modified region 5 in the direction of the normal vector $n_0$. This means that a layer having a thickness t is added over the entire modified region 5 of surface 2, at every point thereof, in the direction of the normal vector $n_0$.

Figure 6B:
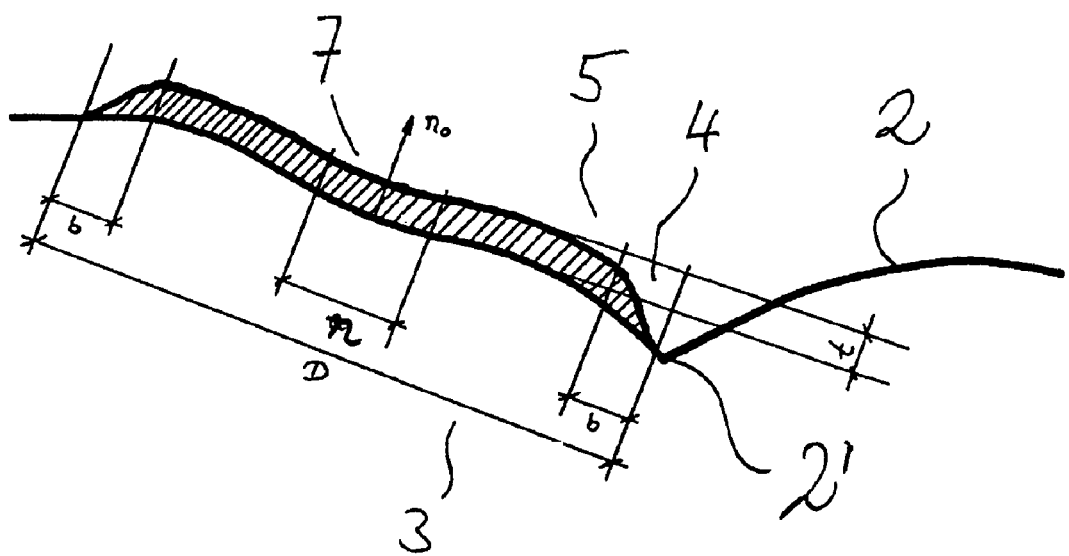
FIG. 6B shows in detail a modification of a second surface made with the tool.

FIG. 6B shows the change in the surface 2 in the region of a fissure that lies surrounding the zone of action 3. A constant change in height t of the surface 2 is carried out over the entire modified region 5 in the direction of the normal vector $n_0$ except in the transition region 4 of extent b. This means that a layer having a thickness t is added over the entire modified region 5 of surface 2, at every point thereof, in the direction of the normal vector $n_0$. The normal vector is calculated from the evaluation region 7, which has an extent n.

In FIG. 7, the transition region 4 between the modified region 5 and the unchanged surface 2 is shown. Within the transition region 4 of extent b, the surface 2 is changed such that both boundaries of the transition region 4 merge smoothly into the respective adjoining regions. For this purpose, the tangent $t_2$ to the surface 2 at the boundary of the zone of action 3, and the tangent $t_5$ to the surface 2 at the inner boundary of the transition region 4 are found and the profile of the surface 2 is defined. Due to the constraints imposed by smooth tangential merging, the surface 2, shown in section, has an inflection point. The transition region can, for example, take the shape of a Gaussian curve.

For the sake of completeness it is pointed out that the direction of tangent $t_5$ is the same as that of tangent $t_6$, which, at the inner boundary of the transition region 4, is displaced by a layer thickness t due to the change in height in the direction of the normal vector $n_0$.

Figure 8A:
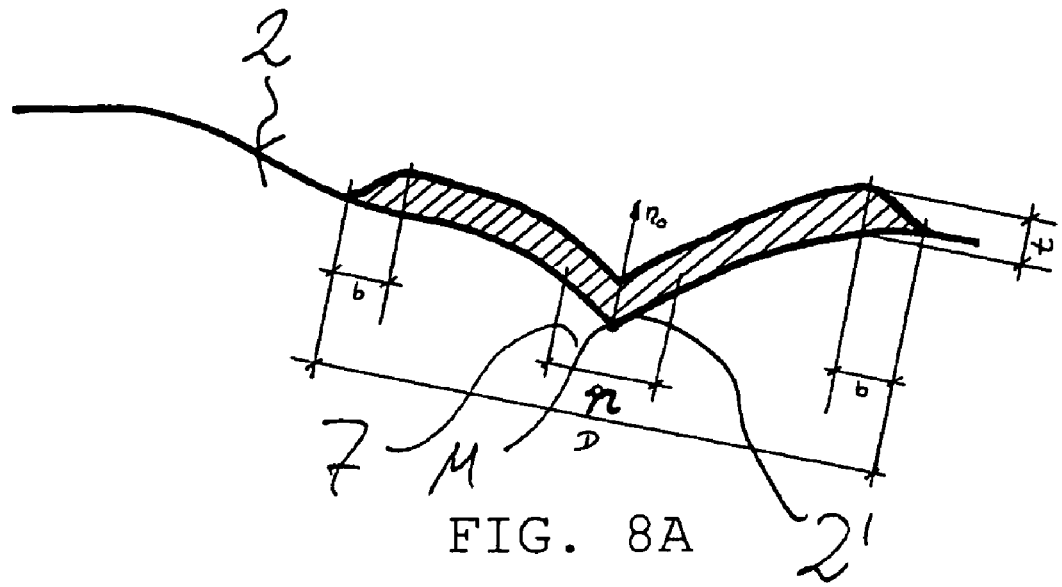
FIG. 8A shows a first profile of a change in a selected region with a varying normal vector.

FIG. 8A shows the results of the tool in a region with a sharply changing normal vector. Such changes occur, for example, near a structural feature in the form of a fissure 2' in a dental prosthetic item. Here again, proceeding from a midpoint M over the zone of action 3, with the exception of a transition region 5, a change of the surface 2 is brought about in which a change in height of constant thickness t is effected in the direction of a normal vector $n_0$. The normal vector $n_0$ was determined over the evaluation region 7, with the fissure 2' lying within the evaluation region.

Figure 8B:
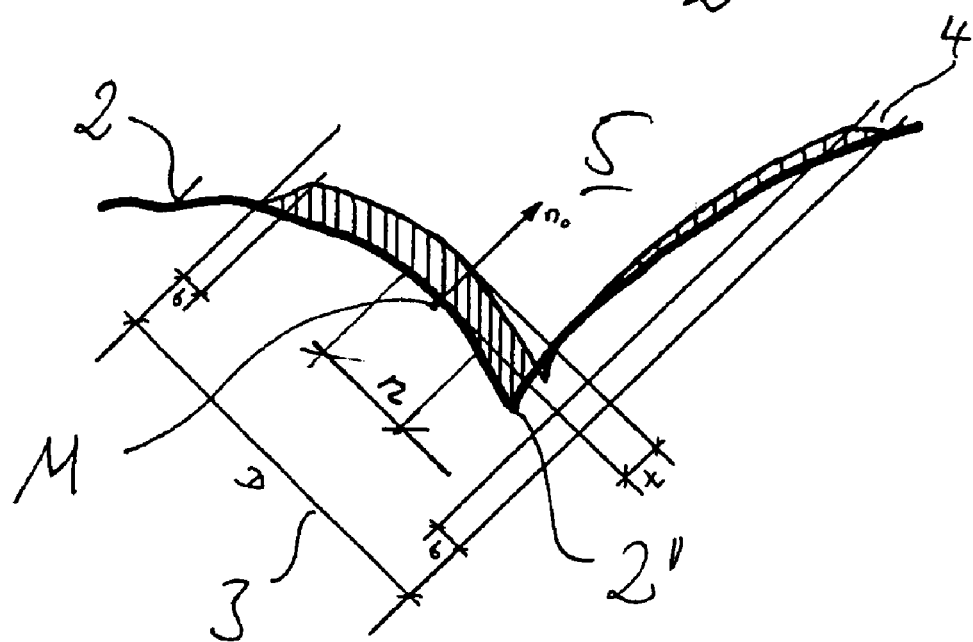
FIG. 8B shows a second profile of a change in a selected region with a sharply varying normal vector.

FIG. 8B shows the results of the tool in a zone of action having a sharply changing normal vector, with the evaluation region lying outside the fissure 2'. Here again, proceeding from the midpoint M over the zone of action 3, with the exception of a transition region 5, a change of the surface 2 is also brought about, in which a change in height of constant thickness t is effected in the direction of a normal vector $n_0$. It appears as if the part on the right-hand side has duplicated itself, but what has actually occurred here is again a shift by approximately the thickness t toward the transition region. There the modified region 5 merges into the transition region 4 and into the surface 2 surrounding the zone of action 3.

One can see from FIGS. 8A and 8B that the fissure 2' substantially remains. This is a decisive advantage of this tool over known free-form tools.

In FIG. 9, a possible relation between the extent D of the zone of action of the tool and the change in height t is shown diagrammatically, for which it always holds that the extent $D_a$ of the selected zone of action is larger than the selected thickness $t_a$. In practice, it has been shown that it is preferable for the extent D of the zone of action to be much larger than the thickness t. One may furthermore note from FIG. 9 that with increasing values of the extent D of the zone of action, the thickness t of the change in height is reduced, so that if the user chooses a large zone of action, the change in height t will be smaller than when the user chooses a smaller zone of action. In practice, however, it has been found that the extent D of the zone of action need not have any influence on the thickness t, and that therefore the thickness t can be independent of the extent D.

The exemplary embodiment is clarified by the following numerical values. For a change in height by a layer thickness t of $10 \times 10^{-6}$ m, one obtains, at a ratio of 1:140, a width of $1400 \times 10^{-6}$ m for the zone of action. In this case, the transition region, at a ratio of 10:1 to the layer thickness, will have a thickness of $100 \times 10^{-6}$ m, whereby a sufficiently fine transition is assured.

In an apparatus for processing a digitized workpiece, especially a three-dimensional model of a dental prosthetic item to be produced therefrom by altering the surface data of the workpiece by means of a tool which acts on a local zone of action (3) on the surface (2), means are provided which, when the tool is applied to the surface in a zone of action (3) of the tool, bring about a change in height of the surface (2), which zone of action (3) includes a modified region (5) showing a change in height that is substantially constant over the zone of action (3) and a transition region (4) in which the surface of the modified region (5) merges into the surface surrounding the zone of action (3).

These means include algorithms for changing the surface data and means for selecting that region of the surface which is to be processed.

This device can further include the features which are necessary for carrying out the method of the invention, as described above.

The invention claimed is:

1. A method of processing a digitized three-dimensional model of a dental prosthetic item in the preparation of said item using a virtual tool, comprising the steps of:
    applying the virtual tool in a local zone of action of a surface of the model so as to change the height of said surface within the local zone of action, said local zone of action having an extent, and said local zone of action including a selected region, corresponding to a location of the virtual tool relative to the surface of said local zone of action,
        a modification region, which contains the selected region and also contains a structural feature of the surface of said local zone of action,
        an outer transition region surrounding the modified region, and having a surface which merges with a surface of the model surrounding said local zone of action; and
        an evaluation region whose area extent has a ratio of 1:5 to 1:200 to the extent of said local zone of action; and
    moving the virtual tool over the selected region to change the height of the surface of said local zone of action, the change in height being substantially constant over the modified region, and being non-constant over the outer transition region, and being substantially everywhere in a direction of a vector, wherein said vector is an average of normal vectors over the evaluation region, and the change in height not removing said structural feature located in the modified region.

2. The method as defined in claim 1, wherein said structural feature is a fissure.

3. A method as defined in claim 1, wherein said tool is applied such that said change in height of said local zone of action bears a ratio to the extent of said local zone of action of at most 1:50.

4. A method as defined in claim 3, wherein said transition region of the local zone of action has a width which bears a ratio to the change in height of from 1:1 to 20:1.

5. A method as defined in claim 1, wherein said change in height comprises the step of addition or removal of material and choosing the direction of said change in height is made possible by selection means.

6. A method as defined in claim 5, wherein the selection of the direction of said change in height is indicated by different representations of the tool.

7. A method as defined in claim 1, wherein said local zone of action of the tool is visibly distinguishable from the representation of the surface of the model.

8. A method as defined in claim 1, wherein a size of said local zone of action is modifiable, and including the step of indicating the size of said local zone of action.

9. A method as defined in claim 8, wherein the change in height diminishes with increasing extent of the local zone of action.

10. A method as defined in claim 1, wherein an amount of change in height is dependent on the extent of said local zone of action.

11. A method as defined in claim 1, wherein said ratio is 1:100 to 1:200.

* * * * *